United States Patent
Kase et al.

(10) Patent No.: US 10,919,834 B2
(45) Date of Patent: Feb. 16, 2021

(54) METHOD FOR PRODUCING (METH)ACRYLIC ACID

(71) Applicant: NIPPON SHOKUBAI CO., LTD., Osaka (JP)

(72) Inventors: Yuki Kase, Hyogo (JP); Toyofumi Sakai, Hyogo (JP); Yasutaka Takemoto, Hyogo (JP); Masashi Mukae, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 16/614,450

(22) PCT Filed: May 22, 2018

(86) PCT No.: PCT/JP2018/019700
§ 371 (c)(1),
(2) Date: Nov. 18, 2019

(87) PCT Pub. No.: WO2018/216699
PCT Pub. Date: Nov. 29, 2018

(65) Prior Publication Data
US 2020/0181056 A1 Jun. 11, 2020

(30) Foreign Application Priority Data
May 25, 2017 (JP) .................................. 2017-103849

(51) Int. Cl.
*C07C 51/44* (2006.01)
*C07C 57/04* (2006.01)

(52) U.S. Cl.
CPC .............. *C07C 51/44* (2013.01); *C07C 57/04* (2013.01)

(58) Field of Classification Search
CPC .................................. C07C 51/44; C07C 57/04
See application file for complete search history.

(56) References Cited

U.S. PATENT DOCUMENTS

| | | | |
|---|---|---|---|
| 2001/0020111 A1 | 9/2001 | Ueno et al. | |
| 2004/0249201 A1* | 12/2004 | Ueno | C07C 51/44 562/545 |
| 2011/0036704 A1* | 2/2011 | Blum | C07C 51/252 203/31 |

FOREIGN PATENT DOCUMENTS

| | | |
|---|---|---|
| JP | 2001-199931 | 7/2001 |
| JP | 2004-359615 | 12/2004 |

OTHER PUBLICATIONS

International Search Report dated Jun. 26, 2018 in International (PCT) Application No. PCT/JP2018/019700.
Office Action dated May 19, 2020 in corresponding Japanese Patent Application No. 2019-520266, with English Translation.

* cited by examiner

*Primary Examiner* — Paul A Zucker
(74) *Attorney, Agent, or Firm* — Wenderoth, Lind & Ponack, L.L.P.

(57) ABSTRACT

A method for producing (meth)acrylic acid comprising: a step of obtaining a (meth)acrylic acid-containing gas by subjecting a (meth)acrylic acid production raw material to a catalytic gas phase oxidation reaction; a step of obtaining a (meth)acrylic acid-containing liquid by bringing the (meth) acrylic acid-containing gas into contact with a collection solvent and/or condensing the (meth)acrylic acid-containing gas by cooling; a step of obtaining crude (meth)acrylic acid by introducing the (meth)acrylic acid-containing liquid into a low-boiling separation column; a step of obtaining purified (meth)acrylic acid and a refining residue containing a glyoxal compound by purifying the crude (meth)acrylic acid; and a step of returning at least a part of the refining residue to the low-boiling separation column; wherein a returning position of the refining residue to the low-boiling separation column is located closer to a bottom side of the low-boiling separation column than a supply port of the (meth)acrylic acid-containing liquid.

6 Claims, 4 Drawing Sheets

[Fig. 1]
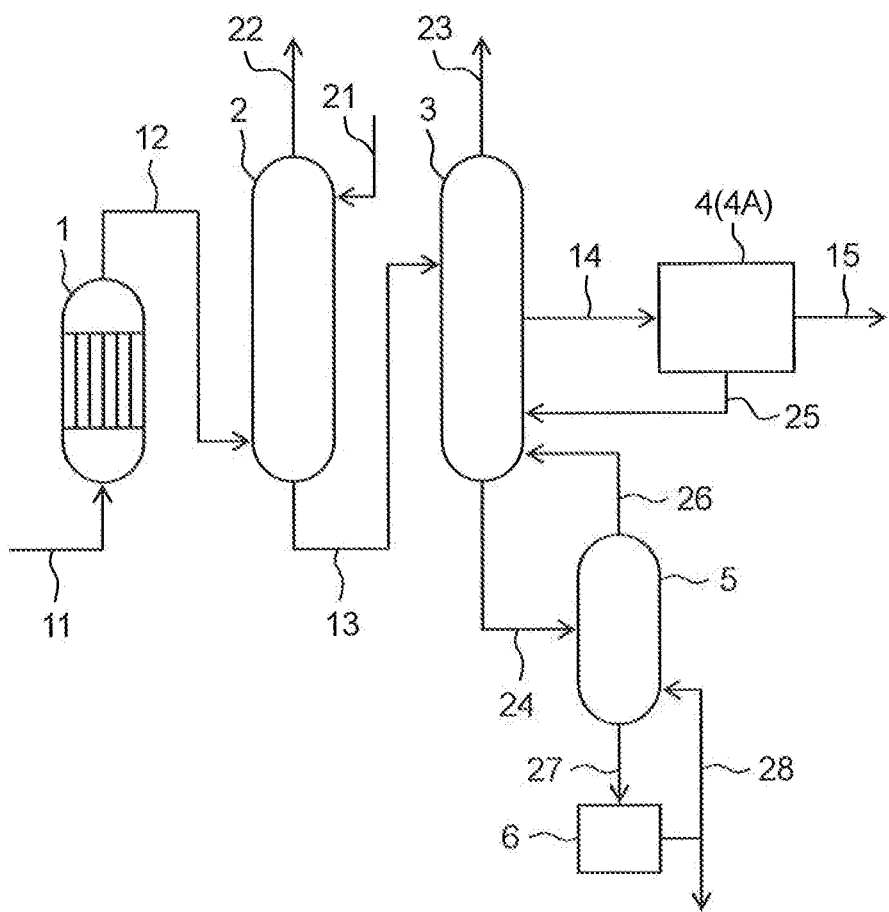

[Fig. 2]
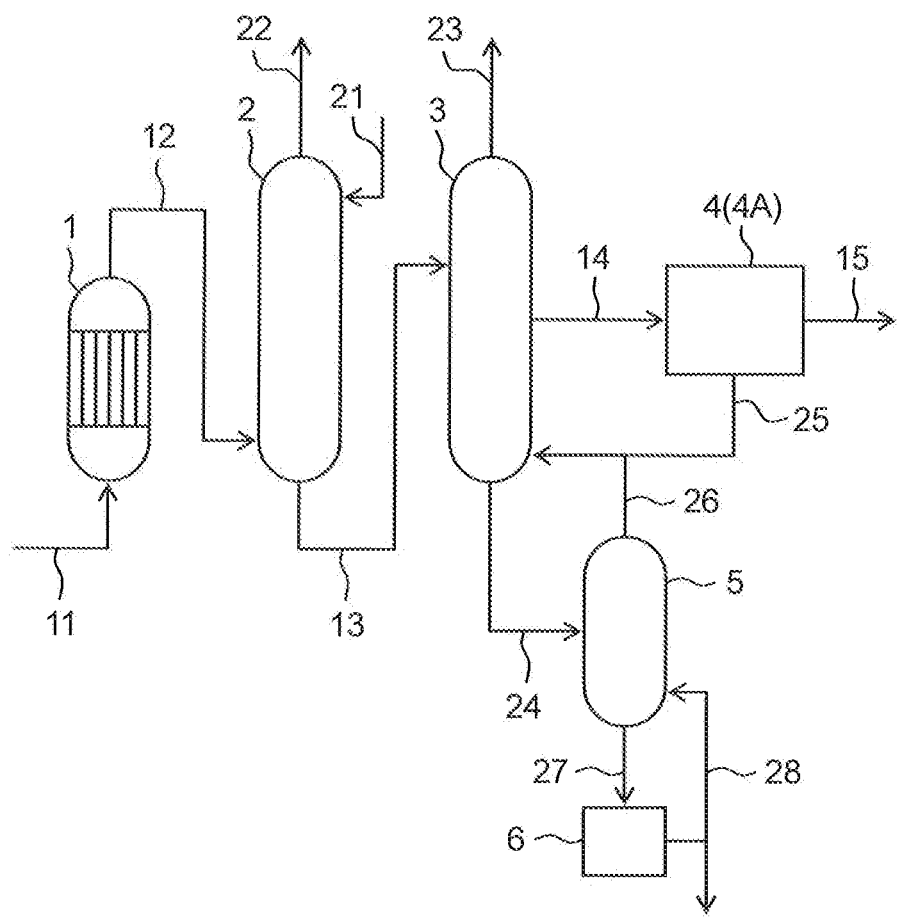

[Fig. 3]
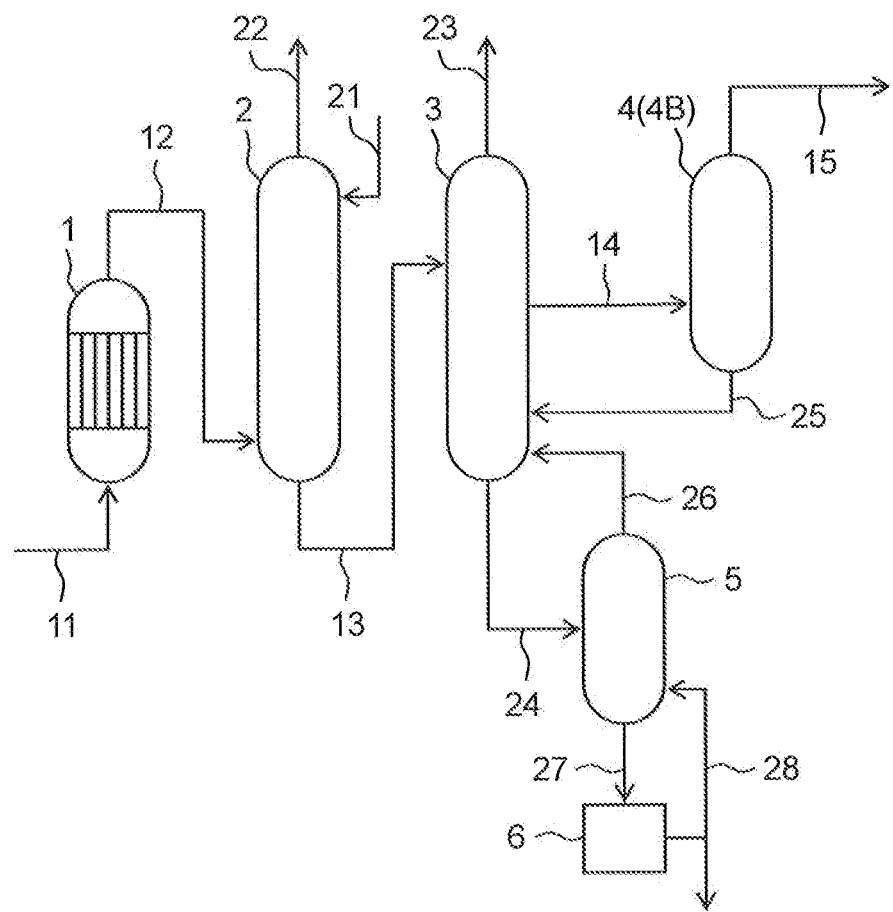

[Fig. 4]
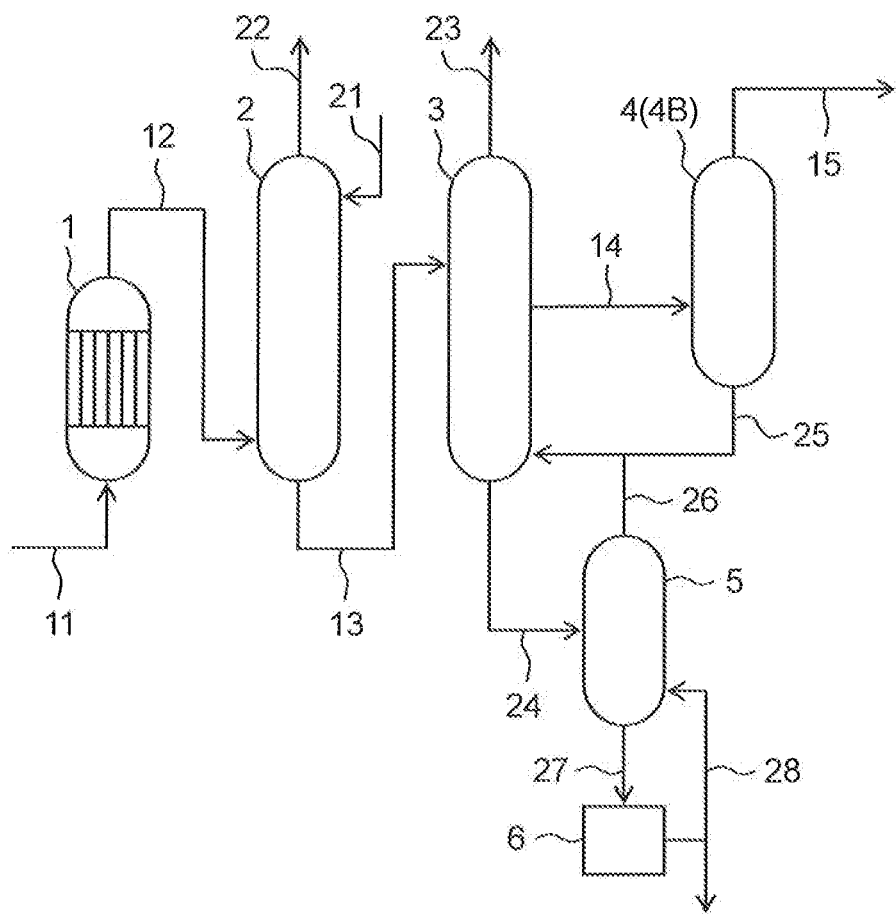

METHOD FOR PRODUCING (METH)ACRYLIC ACID

TECHNICAL FIELD

The present invention relates to a method for producing (meth)acrylic acid, and specifically relates to a method for producing (meth)acrylic acid including the step of purification by distillation.

BACKGROUND ART

Conventionally, a process for producing (meth)acrylic acid by subjecting a (meth)acrylic acid production raw material such as propylene, isobutylene, acrolein or methacrolein to a catalytic gas phase oxidation reaction has been known, and thus obtained (meth)acrylic acid is usually refined by a purification means such as distillation and crystallization. For example, in Patent Literatures 1 and 2, a process for producing (meth)acrylic acid comprising the steps of: obtaining a (meth)acrylic acid-containing gas by subjecting a (meth)acrylic acid production raw material to a catalytic gas phase oxidation reaction; obtaining a (meth)acrylic acid-containing liquid by introducing the (meth)acrylic acid-containing gas into a collection column and bringing it into contact with a collection solvent; distilling the (meth)acrylic acid-containing liquid to obtain crude (meth)acrylic acid; and crystallizing the crude (meth)acrylic acid to obtain purified (meth)acrylic acid.

CITATION LIST

Patent Literature

Patent Literature 1
Japanese Unexamined Patent Application Publication No. 2001-199931
Patent Literature 2
Japanese Unexamined Patent Application Publication No. 2004-359615

SUMMARY OF INVENTION

Technical Problem

In purifying (meth)acrylic acid by a purification means accompanied by heating such as distillation, there is a concern that formation of a polymer of (meth)acrylic acid may affect stable operation of the production facilities. Therefore, in purifying (meth)acrylic acid by distillation, various measures such as appropriate temperature control or addition of a polymerization inhibitor are taken to minimize the formation of a polymer of (meth)acrylic acid. However, as a result of investigations by the present inventors, it has been found that even when such measures are taken, a polymer of (meth)acrylic acid is generated in the distillation column.

The present invention has been achieved in view of the above circumstances, and the object of the present invention is to provide a method for producing (meth)acrylic acid including the step of performing purification by distillation, that can suppress generation of a polymer of (meth)acrylic acid in a distillation column (low-boiling separation column).

Solution to Problem

The present inventors examined cause of the generation of a polymer of (meth)acrylic acid in a low-boiling separation column and have found that: when (meth)acrylic acid is produced by catalytic gas phase oxidation reaction, glyoxal is formed as a by-product, and this glyoxal could be cause of the generation of a polymer of (meth)acrylic acid in the low-boiling separation column. In particular, in a process for producing a chemical substance such as (meth)acrylic acid, there is a case that a refining residue generated in the subsequent refining step is returned to the previous step in order to increase yield as a whole process, and this refining residue contains impurities at a relatively high concentration. In a production process of (meth)acrylic acid, a refining residue containing a glyoxal compound as a impurity at a relatively high concentration can be generated. And when such a refining residue is returned to a low-boiling separation column, generation of a polymer of (meth)acrylic acid caused by a glyoxal compound easily occurs in the low-boiling separation column. Therefore, the present inventors examined the generation of a polymer of (meth)acrylic acid in detail and have found that: in returning the refining residue to the low-boiling separation column, by appropriately setting the returning position of the refining residue, the generation of a polymer of (meth)acrylic acid come to be less likely to occur.

The present invention includes the following inventions.
[1] A method for producing (meth)acrylic acid, the method comprising: a step of obtaining a (meth)acrylic acid-containing gas by subjecting a (meth)acrylic acid production raw material to a catalytic gas phase oxidation reaction; a step of obtaining a (meth)acrylic acid-containing liquid by bringing the (meth)acrylic acid-containing gas into contact with a collection solvent and/or condensing the (meth)acrylic acid-containing gas by cooling; a step of obtaining crude (meth)acrylic acid by introducing the (meth)acrylic acid-containing liquid into a low-boiling separation column; a step of obtaining purified (meth)acrylic acid and a refining residue containing a glyoxal compound by purifying the crude (meth)acrylic acid; and a step of returning at least a part of the refining residue to the low-boiling separation column; wherein a returning position of the refining residue to the low-boiling separation column is located closer to a bottom side of the low-boiling separation column than a supply port of the (meth)acrylic acid-containing liquid.
[2] The method for producing (meth)acrylic acid according to [1], wherein the crude (meth)acrylic acid is introduced into a crystallizer and purified, and the refining residue is obtained as a crystallizing residue.
[3] The method for producing (meth)acrylic acid according to [1] or [2], wherein the crude (meth)acrylic acid is withdrawn from an outlet port at a middle part of the low-boiling separation column, and the returning position of the refining residue to the low-boiling separation column is located closer to the bottom side of the low-boiling separation column than the outlet port at the middle part of the low-boiling separation column.
[4] The method for producing (meth)acrylic acid according to any one of [1] to [3], wherein the returning position of the refining residue to the low-boiling separation column is located at a bottom part of the low-boiling separation column.
[5] The method for producing (meth)acrylic acid according to any one of [1] to [4], wherein the crude (meth)acrylic acid is withdrawn from the outlet port at the middle part of the low-boiling separation column, and a bottom liquid is withdrawn from the bottom part of the low-boiling separation column and introduced into a high-boiling separation column.

[6] The method for producing (meth)acrylic acid according to [5], wherein a bottom liquid is withdrawn from a bottom part of the high-boiling separation column and introduced into a (meth)acrylic acid dimmer decomposition apparatus.

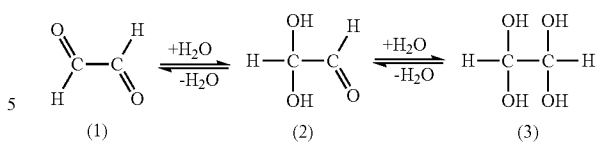

Advantageous Effects of Invention

According to the method for producing (meth)acrylic acid of the present invention, in returning a refining residue to a low-boiling separation column, the refining residue being generated in the step subsequent to the step of using the low-boiling separation column, for increasing yield of (meth)acrylic acid as a whole process, generation of a polymer of (meth)acrylic acid caused by a glyoxal compound can be suppressed by returning the refining residue to the low-boiling separation column from a position located closer to a bottom side of the column than a supply port of the (meth)acrylic acid-containing liquid. Therefore, the low-boiling separation column is able to be operated more stably.

BRIEF DESCRIPTION OF THE DRAWINGS

FIG. 1 shows an example of a schematic flow of a method for producing (meth)acrylic acid of the present invention.

FIG. 2 shows another example of a schematic flow of a method for producing (meth)acrylic acid of the present invention.

FIG. 3 shows another example of a schematic flow of a method for producing (meth)acrylic acid of the present invention.

FIG. 4 shows another example of a schematic flow of a method for producing (meth)acrylic acid of the present invention.

DESCRIPTION OF THE PREFERRED EMBODIMENTS

The present invention relates to a method for producing (meth)acrylic acid comprising the step of performing purification by distillation, and specifically relates to a method for producing (meth)acrylic acid that can suppress generation of a polymer of (meth)acrylic acid caused by a glyoxal compound in the step of purifying (meth)acrylic acid by distillation using a low-boiling separation column, even in the case where a refining residue generated in the subsequent refinement step is returned to the low-boiling separation column, thereby realizing stable operation of the low-boiling separation column.

Glyoxal is a dialdehyde compound represented by the following formula (1), and is produced along with (meth) acrylic acid in a catalytic gas phase oxidation reaction of a (meth)acrylic acid production raw material. Glyoxal (hereinafter also referred to as "glyoxal anhydride") undergoes a hydration reaction in the presence of water by the following equilibrium reaction, whereby glyoxal monohydrate represented by the formula (2) or glyoxal dihydrate represented by the formula (3) is produced. These glyoxal hydrates are high-boiling compounds compared to glyoxal anhydride. In this manner, in a production process of (meth)acrylic acid, the hydrate form of glyoxal compounds changes depending on process temperature or water concentration in its environment.

It is also known that glyoxal hydrates produce glyoxal condensates such as dimers and trimers by dehydration condensation. Such a glyoxal condensate has a low solubility in (meth)acrylic acid solution and is likely to precipitate, and so, it can trigger occurrence of a polymer of (meth) acrylic acid, that may adversely affects stable operation of (meth)acrylic acid production facilities. Therefore, it is desired to appropriately control the form and concentration of a glyoxal compound so that it does not exist at a high concentration in the process.

In the present invention, the "glyoxal hydrate" includes glyoxal hydrates represented by the above formulas (2) and (3) and compounds in which a plurality of glyoxal hydrates are chemically bonded, such as a dehydrated condensate thereof. The "glyoxal compound" includes glyoxal hydrates represented by the above formulas (2) and (3) and compounds in which a plurality of glyoxal hydrates are chemically bonded, such as a dehydrated condensate thereof, in addition to the glyoxal anhydride represented by the above formula (1).

By the way, as the present inventors examined behavior of glyoxal compounds in a production method of (meth)acrylic acid, it was found that in purifying (meth)acrylic acid by distillation, glyoxal compounds are concentrated in a low-boiling separation column and generation of a polymer of (meth)acrylic acid is likely to generate. Comparing an upper part and a lower part of the low-boiling separation column, the lower part of the low-boiling separation column is hotter than the upper part of that, so that water concentration in the lower part of the column is lower than that in the upper part of that. For this reason, proportion of the glyoxal compound existing in the form of anhydride is higher in the lower part of the low-boiling separation column than in the upper part of that, but glyoxal anhydride has a low boiling point, so that it is easily vaporized to move to the upper part of the low-boiling separation column. Meanwhile, since water concentration in the low-boiling separation column is higher in the upper part thereof, proportion of the glyoxal compounds existing in the form of hydrate comes to be higher in the upper part than in the lower part, but glyoxal hydrate which is a high boiling point compound easily moves to the lower part of the low-boiling separation column. In this way, in the low-boiling separation column, since glyoxal compounds move between the upper part and the lower part of the low-boiling separation column while changing its form, the glyoxal compounds is easily concentrated in the low-boiling separation column, thereby easily generating glyoxal condensate. The glyoxal condensate is unlikely to revert to glyoxal hydrate, and therefore, once the glyoxal condensate is generated in the low-boiling separation column, it tends to remain in the low-boiling separation column and precipitate, that can be a trigger of generation of a polymer of (meth) acrylic acid. As a result, generation of a polymer of (meth) acrylic acid due to the glyoxal compound comes to easily occur in the low-boiling separation column.

Thus, in the case where (meth)acrylic acid is purified by distillation, it is difficult to completely separate (meth) acrylic acid and impurities containing a glyoxal compound in a low-boiling separation column, and (meth)acrylic acid obtained from the low-boiling separation column (hereinafter may be referred to as "crude (meth)acrylic acid") comes to contain a glyoxal compound at a certain level of concentration. Therefore, it is preferable that the crude (meth) acrylic acid obtained from the low-boiling separation column is further subjected to another refinement step to remove impurities including a glyoxal compound from the crude (meth)acrylic acid as much as possible; and in such a case, a refining residue containing a glyoxal compound at a relatively high concentration is generated. Here, since this refining residue contains (meth)acrylic acid in a considerable concentration, it is desirable that the refining residue is returned to the previous step such as a low-boiling separation column to increase yield of (meth)acrylic acid as a whole process. However, when the refining residue is returned to the low-boiling separation column, generation of a polymer of (meth)acrylic acid caused by a glyoxal compound in the low-boiling separation column comes to occur more easily by the glyoxal compound contained in the refining residue.

The method for producing (meth)acrylic acid of the present invention comprises the steps of purifying (meth) acrylic acid using a low-boiling separation column and returning a refining residue from the subsequent refining step to the low-boiling separation column, and suppresses generation of a polymer of (meth)acrylic acid caused by a glyoxal compound in the low-boiling separation column, thereby realizing stable operation of the low-boiling separation column. Specifically, the method for producing (meth) acrylic acid comprising: a step of obtaining a (meth)acrylic acid-containing gas by subjecting a (meth)acrylic acid production raw material to a catalytic gas phase oxidation reaction: a step of obtaining a (meth)acrylic acid-containing liquid by bringing the (meth)acrylic acid-containing gas into contact with a collection solvent and/or condensing the (meth)acrylic acid-containing gas by cooling; a step of obtaining crude (meth)acrylic acid by introducing the (meth) acrylic acid-containing liquid into a low-boiling separation column; a step of obtaining purified (meth)acrylic acid and a refining residue containing a glyoxal compound by purifying the crude (meth)acrylic acid; and a step of returning at least a part of the refining residue to the low-boiling separation column; wherein a returning position of the refining residue to the low-boiling separation column is located closer to a bottom side of the low-boiling separation column than a supply port of the (meth)acrylic acid-containing liquid. Hereinafter, the method for producing (meth)acrylic acid of the present invention is explained.

First, in a catalytic gas phase oxidation reaction step, a (meth)acrylic acid production raw material is subjected to a catalytic gas phase oxidation reaction to obtain a (meth) acrylic acid-containing gas. The (meth)acrylic acid production raw material can be used without particular limitation as long as (meth)acrylic acid is formed by reaction, and examples thereof include propane, propylene, (meth)acrolein, isobutylene and others. Acrylic acid can be obtained by, for example, oxidizing propane, propylene or acrolein in one step, or oxidizing propane or propylene via acrolein in two steps. Acrolein is not limited to that obtained by oxidizing propane or propylene, which is used as a raw material, and acrolein may be obtained by dehydrating glycerin of a raw material, for example. Methacrylic acid can be obtained by, for example, oxidizing isobutylene or methacrolein in one step, or oxidizing isobutylene via methacrolein in two steps.

As a catalyst used for the catalytic gas phase oxidation, a conventionally known catalyst can be used. For example, in the case where propylene is used as a raw material for producing acrylic acid, a complex oxide catalyst containing molybdenum and bismuth (molybdenum-bismuth catalyst) is preferably used as the catalyst. In the case where propane or acrolein is used as a raw material for producing acrylic acid, a complex oxide catalyst containing molybdenum and vanadium (molybdenum-vanadium catalyst) is preferably used as the catalyst.

As a reactor for performing the catalytic gas phase oxidation reaction, a fixed bed reactor, a fluidized bed reactor, a moving bed reactor, or the like can be used. Among these, from the viewpoint of excellent reaction efficiency, a multitubular fixed bed reactor is preferably used. In the case where (meth)acrylic acid is produced by oxidizing a (meth) acrylic acid production raw material in two steps, a reactor for performing a first oxidation reaction and a rector for performing a second oxidation reaction are combined or one reactor is divided into a region where the first oxidation reaction is performed and a region where the second oxidation reaction is performed, whereby production of (meth) acrylic acid from a (meth)acrylic acid production raw material may be conducted. In the latter case, for example in a fixed bed reactor, a catalyst for performing the first oxidation reaction may be filled in an inlet side (namely, an introduction side of the (meth)acrylic acid production raw material) of reaction tubes of the fixed bed reactor, and a catalyst for performing the second oxidation reaction may be filled in an outlet side of those.

The reaction for producing the (meth)acrylic acid-containing gas from the (meth)acrylic acid production raw material may be conducted under known reaction conditions. For example, in the case of producing acrylic acid from propylene by oxidation reaction in two steps, a propylene-containing gas is introduced into a reactor together with molecular oxygen, and for example, the first oxidation reaction may be conducted under conditions of reaction temperature of 250° C. to 450° C., reaction pressure of 0 MPaG to 0.5 MPaG and space velocity of 300 $h^{-1}$ to 5000 $h^{-1}$, and then the second oxidation reaction may be conducted under conditions of reaction temperature of 250° C. to 380° C., reaction pressure of 0 MPaG to 0.5 MPaG; and space velocity of 300 $h^{-1}$ to 5000 $h^{-1}$.

The (meth)acrylic acid-containing gas obtained by the catalytic gas phase oxidation reaction step is brought into contact with a collection solvent and/or is condensed by cooling, thereby obtaining a (meth)acrylic acid-containing liquid. In the former case, as the (meth)acrylic acid-containing gas is introduced into a collection column and brought into contact with a collection solvent, (meth)acrylic acid is absorbed into the collection solvent, thereby obtaining the (meth)acrylic acid-containing liquid (Collection step). In the latter case, as the (meth)acrylic acid-containing gas is introduced into a condensation column and cooled, (meth)acrylic acid is condensed, thereby obtaining the (meth)acrylic acid-containing liquid (Condensing step).

The collection column is not particularly limited as long as the (meth)acrylic acid-containing gas can be brought into contact with the collection solvent in the collection column. For example, as the (meth)acrylic acid-containing gas is introduced into a collection column from a lower part of the collection column and the collection solvent is introduced into the collection column from an upper part of the collection column, the (meth)acrylic acid-containing gas comes into countercurrent contact with the collection solvent while rising in the collection column, and (meth)acrylic acid is absorbed by the collection solvent and recovered as the (meth)acrylic acid-containing liquid. As the collection column, for example, a tray column provided with shelves (sieve trays) in the column, a packed column filled with a packing in the column, a wet wall column in which the collection solvent is supplied to the surface of the inner wall of the column, a spray column in which the collection solvent is sprayed into the space in the column or the like can be adopted.

The collection solvent is not particularly limited as long as it can absorb and dissolve (meth)acrylic acid, and for example, diphenyl ether, diphenyl, a mixture of diphenyl ether and diphenyl, water, (meth)acrylic acid-containing water (for example, an aqueous solution containing (meth) acrylic acid obtained in the production process of (meth) acrylic acid), or the like can be used. Among them, water or (meth)acrylic acid-containing water is preferably used as the collection solvent, and more preferably, water or (meth) acrylic acid-containing water containing 50 mass % or more (more preferably 70 mass % or more, even more preferably 80 mass % or more) of water.

Temperature and a supply amount of the collection solvent may be appropriately set so that (meth)acrylic acid contained in the (meth)acrylic acid-containing gas is sufficiently absorbed by the collection solvent, Temperature of the collection solvent is preferably 0° C. or higher, more preferably 5° C. or higher, and preferably 35° C. or lower, more preferably 30° C. or lower, from the viewpoint of increasing collection efficiency of (meth)acrylic acid. Regarding a supply amount of the collection solvent, a liquid gas ratio (L/G) indicated by the ratio of a supply amount (L) of the collection solvent to the collection column with respect to a supply amount (G) of the (meth)acrylic acid-containing gas to the collection column is preferably 2 L/m$^3$ or more, more preferably 3 L/m$^3$ or more, even more preferably 5 L/m$^3$ or more, and preferably 15 L/m$^3$ or less, more preferably 12 L/m$^3$ or less, even more preferably 10 L/m$^3$ or less.

(Meth)acrylic acid absorbed by the collection solvent is withdrawn from the collection column as the (meth)acrylic acid-containing liquid. The (meth)acrylic acid-containing liquid may be withdrawn from, for example, a position below a supply position of the (meth)acrylic acid-containing gas in the collection column (for example, the bottom of the collection column).

It is preferred that the collection column is provided with a circulation line for returning a part of the (meth)acrylic acid-containing liquid discharged from the collection column to the collection column, of which returning position is located above a supply position of the (meth)acrylic acid-containing gas and a discharge position of the (meth)acrylic acid-containing liquid and below a supply position of the collection solvent in the collection column. By returning a part of the (meth)acrylic acid-containing liquid discharged from the collecting column to the collecting column through the circulation line and circulating it, (meth)acrylic acid concentration in the (meth)acrylic acid-containing liquid can be increased. The circulation line is preferably provided with a heat exchanger for cooling (meth)acrylic acid passing through the circulation line.

Meanwhile, in the case where the (meth)acrylic acid-containing liquid is obtained by condensing the (meth) acrylic acid-containing gas, a condensation column is preferably used, and as the condensation column, a heat exchanger having a heat transfer surface can be used, for example. By cooling the (meth)acrylic acid-containing gas via the heat transfer surface, (meth)acrylic acid can be condensed from the (meth)acrylic acid-containing gas, and as a result, the (meth)acrylic acid-containing liquid is obtained. A conventionally known heat exchanger may be used as the heat exchanger, and for example, a plate heat exchanger, a multitubular (shell-and-tube) heat exchanger, a double-pipe heat exchanger, a coil heat exchanger, a spiral plate heat exchanger, or the like can be employed. A plurality of heat exchangers may be connected in series and the (meth)acrylic acid-containing gas may be cooled in multiple stage to perform fractional condensation, thereby recovering the (meth)acrylic acid-containing liquid.

The condensation column may be configured so that the (meth)acrylic acid-containing liquid is obtained from the (meth)acrylic acid-containing gas by bringing the (meth) acrylic acid-containing gas into contact with a condensate. In this case, it is preferable to provide a shelves (sieve trays) in the condensation column or fill the condensation column with a packing to improve contact efficiency between the (meth)acrylic acid-containing gas and the condensate. By using such a condensation column, the (meth)acrylic acid-containing gas is separated and condensed as the (meth) acrylic acid-containing gas is introduced into the condensation column from a lower part of the condensation column and moves from the lower part to an upper part of the condensation column, for example. At this time, the (meth) acrylic acid-containing liquid is withdrawn from a middle stage of the condensation column, substances having a higher boiling point than (meth)acrylic acid is withdrawn from a lower stage of the condensation column and substances having a lower boiling point than (meth)acrylic acid is withdrawn from an upper stage of the condensation column, for example. A part of the condensate withdrawn from each stage of the condensation column may be cooled by a heat exchanger or the like and then returned to the same stage of the condensation column. In general, no liquid medium other than the condensate generated in the condensation column is added to the condensate to be returned to the condensation column.

At the time of obtaining the (meth)acrylic acid-containing liquid from the (meth)acrylic acid-containing gas, a polymerization inhibitor may be added into the collection column or the condensation column in order to suppress polymerization of (meth)acrylic acid. As the polymerization inhibitor, conventionally known polymerization inhibitors can be used, and examples of the polymerization inhibitor includes, for example, quinone compounds such as hydroquinone and methoquinone (p-methoxyphenol); phenothiazine compounds such as phenothiazine, bis-(α-methylbenzyl)phenothiazine, 3,7-dioctylphenothiazine and bis-(α-dimethylbenzyl)phenothiazine; N-oxyl compounds such as 2,2,6,6-tetramethylpiperidinooxyl, 4-hydroxy-2,2,6,6-tetramethylpiperidinooxyl and 4,4',4''-tris-(2,2,6,6-tetramethylpiperidinooxyl)phosphite; copper salt compounds such as copper dialkyl dithiocarbamate, copper acetate, copper naphthenate, copper acrylate, copper sulfate, copper nitrate and copper chloride; manganese salt compounds such manganese dialkyl dithiocarbamate, manganese diphenyl dithiocarbamate, manganese formate, manganese acetate, manganese octanoate and manganese naphtenate; nitroso compounds such as N-nitrosophenyl hydroxylamine or salts thereof, p-nitrosophenol and N-nitrosodiphenylamine or salts thereof; and the like. These polymerization inhibitors may be used alone or in combination of two or more.

(Meth)acrylic acid concentration in the (meth)acrylic acid-containing liquid is not particularly limited; however, it is preferably, for example, 80 mass % or more, more preferably 85 mass % or more, even more preferably 90 mass % or more, and particularly preferably 92 mass % or more. The upper limit of (meth)acrylic acid concentration in the (meth)acrylic acid-containing liquid is not particularly limited, and is usually 97 mass % or less.

The thus obtained (meth)acrylic acid-containing liquid as described above is introduced into a low-boiling separation column to obtain crude (meth)acrylic acid (Low-boiling separation step). Into the low-boiling separation column, all of the obtained (meth)acrylic acid-containing liquid may be introduced, or only a part thereof may be introduced. In the low-boiling separation column, at least a part of a low-boiling fraction is removed from the (meth)acrylic acid-containing liquid, thereby obtaining crude (meth)acrylic acid. The low-boiling fraction means a fraction having a lower boiling point than the crude (meth)acrylic acid, that is, a fraction withdrawn from a top side of the column relative to the crude (meth)acrylic acid in the low-boiling separation column. The low-boiling fraction includes a compound having a lower boiling point than (meth)acrylic acid such as water and acetic acid.

As the low-boiling separation column, a tower-type equipment generally used as a distillation column can be used, and a tray column provided with shelves (sieve trays) in the column (e.g., a perforated plate column and a bubble bell column), or a packed column filled with a packing in the column can be used. The low-boiling separation column has a top part, a middle part and a bottom part, and when the low-boiling separation column is divided in the height direction, the range, with respect to the height direction, in which a plate or a packing is provided is referred to as the middle part, a top side thereto is referred to as the top part, and a bottom side thereto is referred to as the bottom part.

It is preferable that the (meth)acrylic acid-containing liquid is supplied to the low-boiling separation column through a supply port at the middle part thereof. The supply port of the (meth)acrylic acid-containing liquid is preferably provided, for example, in the range of 5% or more and 75% or less of the total theoretical plate number, counted from the top side of the column in the range of from the top part to the bottom part of the low-boiling separation column, and that range is more preferably 10% or more, even more preferably 15% or more, and more preferably 70% or less, even more preferably 65% or less.

The low-boiling fraction is withdrawn from the top side of the column relative to the supply port of the (meth)acrylic acid-containing liquid. The low-boiling fraction is preferably withdrawn from a position in the range of 0% or more to less than 5% of the total theoretical plate number, counted from the top side of the column in the range of from the top part to the bottom part of the low-boiling separation column, and particularly preferably withdrawn from the top part of the column. The low-boiling fraction distilled from the low-boiling separation column is preferably returned to the preceding collection column or condensation column. In returning to the collection column, its position is not particularly restricted, but the low-boiling fraction is preferably returned to, for example, a position in the range of 20% or more and 90% or less, more preferably returned to a positon in the range of 30% or more and 80% or less in the entire length of the collection column, provided that the bottom of the collection column is the start point (0%) and the top of that is the end point (100%).

The crude (meth)acrylic acid is withdrawn from an outlet port provided at the middle part and/or the bottom part of the low-boiling separation column. That is, the crude (meth) acrylic acid is obtained as a fraction (distillate) withdrawn from the middle part of the column and/or as a bottom liquid withdrawn from the bottom part of the column in the low-boiling separation column. The outlet port of the crude (meth)acrylic acid is preferably provided on the bottom side of the column relative to the supply port of the (meth)acrylic acid-containing liquid, and for example, it is provided preferably in the range of 20% or more and 100% or less of the total theoretical plate number, counted from the top side of the column in the range of from the top part to the bottom part of the low-boiling separation column, and that range is more preferably 25% or more, even more preferably 35% or more. The outlet port of the crude (meth)acrylic acid is preferably provided at the middle part of the column, and thereby, the crude (meth)acrylic acid with a reduced content of high-boiling components can be obtained. That is, in this case, since the bottom liquid containing a large amount of high-boiling components are withdrawn from the bottom part of the column, it becomes easy to increase (meth)acrylic acid concentration in the crude (meth)acrylic acid that is withdrawn from the middle part of the column. In this case, the outlet port of the crude (meth)acrylic acid is preferably provided in the range of 90% or less of the total theoretical plate number, counted from the top side of the column in the range of from the top part to the bottom part of the low-boiling separation column, and that range is more preferably 80% or less, even more preferably 70% or less.

A part of the bottom liquid withdrawn from the bottom part of the low-boiling separation column may be returned to the low-boiling separation column after heating with heating means such as a reboiler. At this time, a part of the bottom liquid is preferably returned to the bottom part of the low-boiling separation column, and thereby, temperature adjustment in the low-boiling separation column is facilitated.

In the low-boiling separation column, distillation is preferably performed under conditions that can separate a low-boiling fraction including a collection solvent, acetic acid and the like from the crude (meth)acrylic acid, and it is preferable that temperature and pressure in the low-boiling separation column is appropriately adjusted so that such distillation can be performed. For example, pressure (absolute pressure) at the top of the column is preferably 2 kPa or higher, more preferably 3 kPa or higher, and preferably 50 kPa or lower, more preferably 40 kPa or lower, even more preferably 30 kPa or lower. Temperature at the top of the column is preferably 30° C. or higher, more preferably 40° C. or higher, and preferably 70° C. or lower, more preferably 60° C. or lower. Temperature at the bottom of the column is preferably 70° C. or higher, more preferably 80° C. or higher, and preferably 120° C. or lower, more preferably 110° C. or lower. By performing distillation under such conditions, it becomes easy to obtain the crude (meth)acrylic acid having a reduced concentration of the collection solvent or acetic acid (for example, both water concentration and acetic acid concentration are 1 mass % or less).

In the low-boiling separation column, a polymerization inhibitor may be added for suppressing polymerization of (meth)acrylic acid. As the polymerization inhibitor, various polymerization inhibitors described above can be used.

In the case where the crude (meth)acrylic acid is withdrawn from the middle part of the column, the crude (meth)acrylic acid may be withdrawn as a liquid or may be withdrawn as a vapor. In order to withdraw the crude (meth)acrylic acid as a liquid from the middle part of the column, for example in a tray column, an outlet port may be provided at a position where a shelf is provided or a chimney or the like may be provided to a shelf. When the crude (meth)acrylic acid is withdrawn as a liquid, the crude (meth)acrylic acid can be supplied to the subsequent step without additional processing such as condensation. In the case of withdrawing the crude (meth)acrylic acid as a vapor, the crude (meth)acrylic acid with a relatively low content of impurities is obtained, and therefore, when the crude (meth)acrylic acid is subjected to the subsequent refinement step, refining is facilitated and purified (meth)acrylic acid with high purity is easily obtained. In the low-boiling separation column, a reflux liquid flows down from the top to the bottom of the column and a part of the reflux liquid remains on the shelf, and therefore, by providing the outlet port at a position sufficiently above the shelf, it becomes easy to preferentially withdraw the crude (meth)acrylic acid in the form of vapor while suppressing discharge of the reflux liquid.

In order to properly perform separation and purification by distillation in the low-boiling separation column and facilitate withdrawing the crude (meth)acrylic acid as a vapor from the middle part of the column, it is preferable to control the pressure in the low-boiling separation column as satisfying the following inequalities: pressure at the bottom part of the column>pressure at the middle part of the column>pressure at the top part of the column. For example, the pressure at the top part of the low-boiling separation column is adjusted to an optimum range for distillation by a decompression device, and then the pressure at the top part of the column and the pressure at the middle part of the column are controlled by the decompression device so that the pressure at the middle part of the column is higher than the pressure at the top part of the column. By setting the pressure difference in the low-boiling separation column in this manner, it becomes easy to withdraw the crude (meth)acrylic acid from the middle part of the column as a vapor while properly performing distillation in the low-boiling separation column. The pressure at the middle part of the column relative to the pressure at the top part of the column may be appropriately determined depending on a withdrawing position at the middle part of the column, a withdrawing amount from the middle part of the column, an amount of impurities contained, and the like. For example, the following operation may be carried out that: distillation is performed so that the pressure in the middle part of the column is preliminarily higher than the pressure at the top part of the column, each pressure is controlled based on the composition and distillation amount of the crude (meth)acrylic acid withdrawn from the middle part of the column, and a preferable differential pressure between the top part and the middle part of the column is set.

In the distillation of the (meth)acrylic acid-containing liquid, an azeotropic solvent may be used or may not be used. However, in the case where (meth)acrylic acid concentration in the (meth)acrylic acid-containing liquid is 80 mass % or more, it is preferable that an azeotropic solvent is not used, since a low-boiling fraction is easily removed without using an azetropic solvent.

(Meth)acrylic acid concentration in the crude (meth)acrylic acid obtained from the low-boiling separation column is not particularly limited as long as it is higher than that of the (meth)acrylic acid-containing liquid; however, it is preferably, for example, 80 mass % or more, more preferably 85 mass % or more, even more preferably 90 mass % or more, and particularly preferably 92 mass % or more. The upper limit of the (meth)acrylic acid concentration in the crude (meth)acrylic acid is not particularly limited, and is usually less than 99.5 mass %. In addition, the concentration of a glyoxal compound in the crude (meth)acrylic acid is usually about 100 ppm by mass or more and 2000 ppm by mass or less.

The crude (meth)acrylic acid obtained by the low-boiling separation step is subjected to a refining step. In the refining step, the crude (meth)acrylic acid is purified, thereby obtaining purified (meth)acrylic acid and a refining residue containing a glyoxal compound. The refining residue has a lower (meth)acrylic acid concentration than the crude (meth)acrylic acid. The concentration of a glyoxal compound is usually higher in the refining residue than that in the crude (meth)acrylic acid, and higher in the crude (meth)acrylic acid than that in the purified (meth)acrylic acid. For example, the concentration of a glyoxal compound in the purified (meth)acrylic acid is less than 500 ppm by mass, while the concentration of a glyoxal compound in the refining residue is 500 ppm by mass or more and 3000 ppm by mass or less.

The purification means employed in the refining step is not particularly limited as long as the purified (meth)acrylic acid and the refining residue containing a glyoxal compound are obtained. Examples of the purification means include crystallization, distillation (including fractional distillation), stripping, extraction and others, and a plurality of those may be combined. In the present invention, as described later, the thus obtained refining residue is returned to the low-boiling separation column.

In the case where distillation is employed as the purification means, the above-described tower-type equipment generally used as a distillation column can be used. In purifying by distillation, the purified (meth)acrylic acid is withdrawn from a top side of the distillation column, and the refining residue is obtained from a bottom part of the column as a distillation residue.

Regarding operating conditions of the distillation column when the refining step is performed by distillation, pressure (absolute pressure) at the top of the column is preferably 0 kPa or higher, more preferably 3 kPa or higher, and preferably 50 kPa or lower, more preferably 40 kPa or lower, even more preferably 30 kPa or lower, for example. Temperature at the top of the column is preferably 30° C. or higher, more preferably 40° C. or higher, and preferably 70° C. or lower, more preferably 60° C. or lower. Temperature at the bottom of the column is preferably 70° C. or higher, more preferably 80° C. or higher, and preferably 120° C. or lower, more preferably 110° C. or lower.

In the present invention, it is preferable to employ crystallization as the purification means. In this case, the crude (meth)acrylic acid is introduced into a crystallizer and purified, and the refining residue is obtained as a crystallizing residue. By adopting crystallization as the purification means, problems caused by glyoxal compounds are less likely to occur in the refining step, since the crude (meth)acrylic acid is not disposed under a high temperature condition as compared to the case where the purification is carried out by distillation. Further, by adopting crystallization as the purification means, glyoxal compounds contained in the crude (meth)acrylic acid are easily transferred to the crystallizing residue (non-crystalline residue) at a high ratio when the crude (meth)acrylic acid is crystallized, and thus, it becomes easy to obtain the purified (meth)acrylic acid having a low glyoxal compound concentration. In this case, the crystallizing residue comes to contain a relatively high concentration of glyoxal compounds, however in the present invention, even when returning such a crystallizing residue to the low-boiling separation column as described later, generation of a polymer of (meth)acrylic acid caused by a glyoxal compound in the low-boiling separation column can be suppressed.

In the crystallization step, the crude (meth)acrylic acid is introduced into a crystallizer, and purified (meth)acrylic acid and a crystallizing residue containing a glyoxal compound are obtained. Crystallization may be performed batchwise or continuously.

In a batch crystallization operation, (meth)acrylic acid is crystallized by cooling the crude (meth)acrylic acid, and purified (meth)acrylic acid is obtained by collecting the crystallized (meth)acrylic acid. Meanwhile, non-crystalline residue that is generated in cooling the crude (meth)acrylic acid is discharged from the crystallizer as a crystallizing residue. (Meth)acrylic acid crystallized in the crystallization step (namely, a (meth)acrylic acid crystal) is incited to obtain a (meth)acrylic acid melt, that is preferably recovered as the purified (meth)acrylic acid. In addition, in order to increase purity of the (meth)acrylic acid melt to be obtained, it is preferable that the (meth)acrylic acid crystals are first partially melted (sweated), whereby impurities present between the crystals or on the surface of the crystals are washed away, and then the purified (meth)acrylic acid is recovered by melting the remaining (meth)acrylic acid crystals. At this time, the former melt, that is, a sweated solution obtained by partially melting the (meth)acrylic acid crystal is preferably discharged from the crystallizer as a crystallizing residue.

In a continuous crystallization operation, for example, the crude (meth)acrylic acid is continuously supplied to a crystallizer and cooled to crystallize (meth)acrylic acid, a slurry composed of (meth)acrylic acid crystals and a mother liquor is continuously discharged from the crystallizer, and the slurry is supplied to a washing column to continuously separate the (meth)acrylic acid crystals from the mother liquor while washing.

The crystallizer is not particularly limited as long as it is capable of crystallizing the crude (meth)acrylic acid. Examples of the crystallizer include, for example, a crystallizer having a heat transfer surface, wherein (meth)acrylic acid-containing solution is crystallized and/or melted by heat-exchange via the heat transfer surface. In this case, when a cooling medium is supplied to one side of the heat transfer surface and the crude (meth)acrylic acid is supplied to the other side of the heat transfer surface, the (meth) acrylic acid-containing solution is cooled by heat-exchange via the heat transfer surface and (meth)acrylic acid is crystallized. In a batch crystallization operation, a heating medium is supplied to the one side of the heat transfer surface and the crystallized (meth)acrylic acid is heated by heat-exchange via the heat transfer surface and the (meth) acrylic acid melt is obtained. Melting of (meth)acrylic acid may be performed by heating the same heat transfer surface used for crystallization, or the crystallized (meth)acrylic acid is collected and the collected (meth)acrylic acid crystal may be heated via another heat transfer surface which is different from one used for crystallization. As a crystallizer having a heat transfer surface, an apparatus generally used as a heat exchanger can be employed. For example, a plate heat exchanger, a multitubular (shell-and-tube) heat exchanger, a double-pipe heat exchanger, a coil heat exchanger, a spiral plate heat exchanger, or the like can be employed.

As a batch-type crystallization apparatus, for example, a layer crystallization apparatus (dynamic crystallizer) manufactured by Sulzer Chemtech Ltd., a static crystallization apparatus manufactured by BEFS PROKEM, or the like can be used.

As a continuous crystallizer, a crystallization apparatus in which a crystallization part, a solid-liquid separation part and a crystal purification part are united (for example, a BMC (Backmixing Column Crystallizer) apparatus); a crystallization apparatus in combination with a crystallization part (e.g., CDC crystallization apparatus (Cooling Disc Crystallizer) manufactured by GOUDA) or a DC crystallization apparatus (Drum Crystallizer) manufactured by GEA, a solid-liquid separation part (e.g., a belt filter or a centrifugal separator), and a crystal purification part (e.g., KCP refiner (Kureha Crystal Purifier) manufactured by Kureha Engineering Co., Ltd. or a WC (Wash Column) refiner manufactured by GEA Inc.); or the like can be used.

In the batch crystallization operation, it is preferable that crystallizing and melting are alternately repeated several times to obtain the purified (meth)acrylic acid with higher purity. That is, it is preferable that the crude (meth)acrylic acid is crystallized and melted to obtain the (meth)acrylic acid melt, and further thus obtained (meth)acrylic acid is crystallized and melted once or more, thereby obtaining the purified (meth)acrylic acid. The number of times of crystallizing and melting may be appropriately determined in consideration of purity of the obtained purified (meth)acrylic acid obtained and the production efficiency (production amount per unit time).

In the production method of the present invention, the thus obtained refining residue is returned to the low-boiling separation column. In the case where crystallizing and melting are repeated a plurality of times in the crystallization step, it is preferable to return all or part of the crystallizing residue (refining residue) obtained by at least the first crystallization operation to the low-boiling separation column. In the case of returning a part of the crystallizing residue (refining residue) to the low-boiling separation column, it is preferable that the remaining crystallizing residue (refining residue) is supplied to a high-boiling separation step described later. This is because the crystallizing residue obtained by the first crystallization operation has a particularly lower (meth)acrylic acid concentration and contains more impurities than the crude (meth)acrylic acid supplied to the crystallizer. The crystallizing residue obtained by second or later (for example, $k^{th}$ wherein k is an integer of 2 or more) crystallization operation may be subjected to the earlier (namely, $k-1^{th}$ or less ordinal) crystallization operation.

Temperature of the heat transfer surface at the time of crystallizing the crude (meth)acrylic acid (in the case of using a cooling medium, the temperature of the cooling medium) is not particularly limited as long as it is less than the melting point of (meth)acrylic acid. Temperature of the heat transfer surface at the time of melting the (meth)acrylic acid crystal (in the case of using a heating medium, the temperature of the heating medium) is not particularly limited as long as it exceeds the melting point of (meth) acrylic acid, but it is preferably 40° C. or lower and more preferably 35° C. or lower, since (meth)acrylic acid is polymerized at high temperature.

In the refining step, a polymerization inhibitor may be added, in order to suppress polymerization of (meth)acrylic acid. As the polymerization inhibitor, various polymerization inhibitors described above can be used.

The purified (meth)acrylic acid obtained in the refining step may be further purified by any purification means, but it is preferably handled as product (meth)acrylic acid without further purification. (Meth)acrylic acid concentration of the purified (meth)acrylic acid is, for example, preferably 99.5 mass % or more, more preferably 99.7 mass % or more, and even more preferably 99.9 mass % or more. The purified (meth)acrylic acid may be used as a raw material for producing (meth)acrylic acid ester, sodium polyacrylate and others.

In the method for producing (meth)acrylic acid of the present invention, at least a part of the refining residue obtained as described above is returned to the low-boiling separation column (Returning step). The refining residue contains (meth)acrylic acid at a considerable concentration, and the (meth)acrylic acid concentration of the refining residue can be higher than that of the (meth)acrylic acid-containing liquid introduced into the low-boiling separation column. Therefore, by returning the refining residue to the low-boiling separation column, yield of (meth)acrylic acid as a whole process can be increased. In returning the refining residue to the low-boiling separation column in this way, it is easy from the facilities aspect to introduce the refining residue into a supply line connected to the supply port for the (meth)acrylic acid-containing liquid of the low-boiling separation column. In this case, the refining residue is introduced into the low-boiling separation column through the supply port of the (meth)acrylic acid-containing liquid; however, according to the inventors' investigation, when the refining residue is returned to the low-boiling separation column in such a manner, generation of a polymer of (meth)acrylic acid caused by a glyoxal compound easily occurs in the low-boiling separation column, and for solving this, it has been cleared that it is effective to return the refining residue to a position which is located closer to the bottom side of the low-boiling separation column than the supply port of the (meth)acrylic acid-containing liquid.

In the production method of the present invention, by returning the refining residue to the position which is located closer to the bottom side of the low-boiling separation column than the supply port of the (meth)acrylic acid-containing liquid, the glyoxal compound contained in the refining residue tends to undergoes more thermal history in the low-boiling separation column, and so it is considered that the ratio of the glyoxal compound changing to another compound that does not affect the generation of a polymer of (meth)acrylic acid is increased. As a result, the concentration of a glyoxal compound in the column is decreased, compared with the case where the refining residue is returned to the low-boiling separation column through the supply port of the (meth)acrylic acid-containing liquid, and the generation of a polymer caused by the glyoxal compound is thought to be difficult to occur. As explained in the examples described later, it was obtained the following result that: when the refining residue was returned to the position which was located closer to the bottom side of the low-boiling separation column than the supply port of the (meth)acrylic acid-containing liquid, the conversion ratio of a glyoxal compound in the low-boiling separation column was increased and the generation of a polymer of (meth) acrylic acid was not observed in the low-boiling separation column; and hence, this result indicates that the glyoxal compound is changed to another compound that does not affect the generation of a polymer of (meth)acrylic acid.

The conversion ratio of a glyoxal compound is determined by the formula: [[{(amount of a glyoxal compound in the (meth)acrylic acid-containing liquid introduced into the low-boiling separation column)+(amount of a glyoxal compound in the refining residue returned to the low-boiling separation column)+(amount of a glyoxal compound returned to the low-boiling separation column in other routes)}−{(amount of a glyoxal compound in the crude (meth)acrylic acid withdrawn from the middle part of the low-boiling separation column)+(amount of a glyoxal compound in the bottom liquid withdrawn from the bottom part of the low-boiling separation column)+(amount of a glyoxal compound in the low-boiling fraction withdrawn from the top part of the low-boiling separation column)}]/{(amount of a glyoxal compound in the (meth)acrylic acid-containing liquid introduced into the low-boiling separation column)+ (amount of glyoxal compound in the refining residue returned to low-boiling separation column)+(amount of a glyoxal compound returned to the low-boiling separation column in other routes)}]×100, and it represents the ratio of sum of the amount of a glyoxal compound accumulated in the low-boiling separation column and the amount of a glyoxal compound changed to another compound in the low-boiling separation column with respect to the amount of a glyoxal compound supplied to the low-boiling separation column. In the above formula, the amount of a glyoxal compound means the total amounts (mass basis) of glyoxal anhydride, glyoxal hydrate and glyoxal condensate. In the case of continuous operation, the amount of a glyoxal compound can be calculated using the amount (mass basis) of a glyoxal compound in each liquid per unit time. In addition, examples of the "amount of a glyoxal compound returned to the low-boiling separation column in other routes" includes the amount of a glyoxal compound in a distillate which is discharged a high-boiling separation column and returned to the low-boiling separation column, as described later. The conversion ratio of a glyoxal compound is, for example, preferably 8% or more, more preferably 10% or more, and even more preferably 15% or more.

In the returning step, from the viewpoint of increasing the ratio of changing the glyoxal compound to another compound that does not affect the generation of a polymer of (meth)acrylic acid, the refining residue is preferably returned to a position being more closer to the bottom side of the low-boiling separation column, and specifically, it is returned to a position preferably in the range of 30% or more and 100% or less of the total theoretical plate number, counted from the top side of the column in the range of from the top part to the bottom part of the low-boiling separation column, and that range is more preferably 50% or more, even more preferably 70% or more, and still even more preferably 90% or more. The refining residue is particularly preferably returned to the bottom part of the low-boiling separation column, and specifically, it is preferably returned to a liquid in the bottom part of the low-boiling separation column.

Conventionally, returning the refining residue to the bottom side of the low-boiling separation column as described above has not been basically done. The reason for this is that, in the low-boiling separation column, the closer to the bottom, the higher the temperature, so that Michael addition reaction of (meth)acrylic acid is likely to occur, and a polymer of (meth)acrylic acid has been thought to be easily generated due to polymerization of (meth)acrylic acid. In addition, in the case where a polymerization inhibitor is contained in the refining residue, when the refining residue is returned to the bottom side of the low-boiling separation column, the polymerization inhibitor contained in the refining residue does not come to contribute to prevention of polymerization so much, and so there was a situation that it was inefficient from the viewpoint of polymerization prevention. Furthermore, in the case where the refining residue contains a large amount of low-boiling components, when such a refining residue is returned to the bottom side of the low-boiling separation column, flashing easily occurs in the low-boiling separation column and there is a possibility that the low-boiling separation column cannot be stably operated, that was not necessarily preferable. In spite of such a situation, the present inventors had studied and found that: when the returning position of the refining residue to the low-boiling separation column is appropriately set and the refining residue is returned to the bottom side of the low-boiling separation column, the ratio of a glyoxal compound converted to another compound that does not affect a polymer of (meth)acrylic acid is increased in the low-boiling separation column, and the generation of a polymer of (meth)acrylic acid in the low-boiling separation column comes to be hard to happen.

As described above, when the refining residue is returned to the bottom side of the low-boiling separation column, (meth)acrylic acid contained in the refining residue undergoes more thermal history in the low-boiling separation column, and as a result, Michael addition reaction of (meth) acrylic acid is likely to occur. Therefore, from the viewpoint of easily obtaining the crude (meth)acrylic acid with higher purity, it is preferable that the crude (meth)acrylic acid is withdrawn from the middle part of the low-boiling separation column as well as the bottom liquid is withdrawn from the bottom part of the low-boiling separation column to be introduced into a high-boiling separation column (High-boiling separation step).

The bottom liquid of the low-boiling separation column contains (meth)acrylic acid at a considerable concentration and further contains a large amount of components having higher boiling point than (meth)acrylic acid, such as Michael adducts and maleic acid, and therefore, when the bottom liquid of the low-boiling separation column is introduced into the high-boiling separation column and distilled, a (meth)acrylic acid-containing distillate having reduced high-boiling components can be obtained. This distillate is preferably returned to the low-boiling separation column, and thereby, yield of (meth)acrylic acid as a whole process can be increased.

As the high-boiling separation column, the above-described tower-type equipment such as a tray column and a packed column can be used. In the high-boiling separation column, distillation is preferably performed under conditions of: theoretical plate number of 1 to 20, pressure (absolute pressure) of 1 kPa to 50 kPa, and column bottom temperature of 120° C. or lower. From the high-boiling separation column, it is preferable to withdrawn the distillate from the top part of the column and return it to the low-boiling separation column. This distillate may also contain a glyoxal compound. Since the distillate withdrawn from the high-boiling separation column contains high-boiling components at a certain level of concentration, the distillate from the high-boiling separation column is preferably returned to the bottom part of the low-boiling separation column, and thereby, it becomes easy to increase purity of the crude (meth)acrylic acid obtained from the low-boiling separation column. In the present invention, the refining residue containing a glyoxal compound may be mixed with the distillate from the high-boiling separation column and returned to the low-boiling separation column; and by returning the refining residue to the low-boiling separation column in this manner, local increase in concentration of a glyoxal compound in the low-boiling separation column can be mitigated.

From the bottom of the high-boiling separation column, a bottom liquid in which high-boiling components such as Michael adducts are concentrated can be obtained. Since the Michael adduct of (meth)acrylic acid can be reverted to (meth)acrylic acid by thermal decomposition, it is preferable that the bottom liquid of the high-boiling separation column is introduced into a (meth)acrylic acid dimer decomposition apparatus. And the liquid obtained from the (meth)acrylic acid dimer decomposition apparatus is preferably returned to the high-boiling separation column.

The (meth)acrylic acid dimer decomposition apparatus is composed of a pyrolysis tank, and the bottom liquid of the high-boiling separation column is heated at the (meth) acrylic acid dimer decomposition apparatus at a temperature of 120° C. or higher and 220° C. or lower (preferably 140° C. or higher and 200° C. or lower), whereby Michael adduct contained in the bottom liquid can be decomposed. A retention time of the pyrolysis tank (pyrolysis tank capacity $(m^3)$/amount of a waste oil $(m^3/h)$) varies depending on the pyrolysis temperature, but usually it can be appropriately adjusted between 0.1 hours and 60 hours, and is preferably 5 hours or longer, more preferably 15 hours or longer, and preferably 50 hours or shorter, more preferably 40 hours or shorter. For accelerating the decomposition of the Michael adduct, it is preferable that a decomposition catalyst such as an alkali metal salt, an alkaline earth metal salt or an N-oxyl compound described in Japanese Unexamined Patent Application Publication No. 2003-89672 is added to the pyrolysis tank. In particular, when an N-oxyl compound is used as a polymerization inhibitor in the low-boiling separation column or the preceding collection or condensation column, it can also act as a decomposition catalyst for Michael adducts, that is preferable.

The bottom liquid of the high-boiling separation column may be heated by a thin film evaporator provided at the bottom of the high-boiling separation column, or a common heat exchanger such as a multitubular heat exchanger, a plate heat exchanger and a spiral plate heat exchanger may be provided and the bottom liquid may be heated by the heat exchanger. As necessary, a bottom liquid of the thin film evaporator or a discharged liquid of the heat exchanger may be introduced into the (meth)acrylic acid dimer decomposition apparatus (the pyrolysis tank). When returning a distillate from the (meth)acrylic acid dimer decomposition apparatus to the high-boiling separation column, it may be returned to the high-boiling separation column via the thin film evaporator or the heat exchanger.

In the case where the high-boiling separation column or the like is installed as described above, the above-described refining residue containing a glyoxal compound may be returned to the low-boiling separation column via a purification apparatus such as the high-boiling separation column; however, it is preferably returned to the low-boiling separation column without a purification apparatus such as a high-boiling separation column. That is, it is preferable that the refining residue is returned to the low-boiling separation column without further refinement. This is because when the refining residue is returned to the high-boiling separation column, (meth)acrylic acid contained in the refining residue is likely to undergoes an excessive thermal history and a large amount of (meth)acrylic acid polymer or Michael adducts tends to be produced, and as a result, recovery efficiency of (meth)acrylic acid may be reduced or a processing amount of the (meth)acrylic acid dimer decomposition apparatus may increase, thereby causing needs of an additional decomposition apparatus. Moreover, concentration of impurities occurs in the high-boiling separation column, and the (meth)acrylic acid concentration in the distillate discharged from the high-boiling separation column tends to decrease. However, even in the case of returning the refining residue to the low-boiling separation column without further refinement, it is permitted to temporarily store the refining residue in a tank.

Next, examples of an embodiment of a method for producing (meth)acrylic acid of the present invention is explained with reference to FIGS. 1 to 4. However, the method for producing (meth)acrylic acid of the present invention is not limited to the embodiments shown in the drawing.

In a process flow shown in FIG. 1, first, a (meth)acrylic acid production raw material 11 is introduced into a reactor 1 and subjected to a catalytic gas phase oxidation reaction, thereby obtaining a (meth)acrylic acid-containing gas 12. Then, the (meth)acrylic acid-containing gas 12 is introduced into a collection column 2 to obtain a (meth)acrylic acid-containing liquid 13. In the collection column 2, the (meth)acrylic acid-containing gas 12 is introduced from a lower part of the collection column 2 while a collection solvent 21 is supplied from an upper part of the collection column 2, whereby the (meth)acrylic acid-containing gas 12 is brought into contact with the collection solvent 21 to obtain the (meth)acrylic acid-containing liquid 13. The obtained (meth)acrylic acid-containing liquid 13 is discharged from a bottom of the collection column 2. A part of an exhaust gas 22 discharged from a top of the collection column 2 is returned to an inlet of the reactor 1 as a recycled gas.

The obtained (meth)acrylic acid-containing liquid 13 is introduced into a low-boiling separation column 3 to obtain crude (meth)acrylic acid 14. In the low-boiling separation column 3, the (meth)acrylic acid-containing liquid 13 is introduced from a supply port provided at a middle part of the column and a low-boiling fraction 23 is distilled from a top of the column, whereby crude (meth)acrylic acid 14 having a reduced amount of low-boiling components such as water and acetic acid is obtained. The low-boiling fraction 23 is preferably returned to the collection column 2 since it may possibly contain the collection solvent used in the collection column 2, but it may be transferred (returned) to any other step or may be discharged out of the system as waste oil. In FIG. 1, the crude (meth)acrylic acid 14 is withdrawn from the middle part of the low-boiling separation column 3, but the crude (meth)acrylic acid 14 may be withdrawn from a bottom part of the low-boiling separation column 3.

The crude (meth)acrylic acid 14 withdrawn from the low-boiling separation column 3 is introduced into a purification apparatus 4 to obtain purified (meth)acrylic acid 15 and a refining residue 25 containing a glyoxal compound. Examples of the purification apparatus 4 include a crystallizer, a distillation column, a stripping column, an extraction column and others, and in FIG. 1, a crystallizer 4A is used. In this case, the refining residue 25 is obtained as a crystallizing residue (that is, an uncrystallized residue when the crude (meth)acrylic acid is cooled).

The refining residue 25 is returned to a position which is located closer to a bottom side of the low-boiling separation column 3 than the supply port of the (meth)acrylic acid-containing liquid, and in FIG. 1, it is returned to the middle part of the low-boiling separation column 3. By returning the refining residue 25 to the position which is located closer to the bottom side of the low-boiling separation column 3 than the supply port of the (meth)acrylic acid-containing liquid, generation of a polymer of (meth)acrylic acid caused by a glyoxal compound in the low-boiling separation column 3 can be suppressed.

From the bottom part of the low-boiling separation column 3, a bottom liquid 24 is withdrawn and preferably introduced into a high-boiling separation column 5, and a distillate 26 from the high-boiling separation column 5 is preferably returned to the low-boiling separation column 3.

When the bottom liquid 24 of the low-boiling separation column 3 is purified by distillation in the high-boiling separation column 5 and returned to the low-boiling separation column 3 in this manner, yield of (meth)acrylic acid as a whole process can be increased. The refining residue 25 may be returned to the low-boiling separation column 3 together with the distillate 26 of the high-boiling separation column 5.

It is preferable that a bottom liquid 27 of the high-boiling separation column 5 is introduced into a (meth)acrylic acid dirtier decomposition apparatus 6 and a liquid 28 obtained from the (meth)acrylic acid dimer decomposition apparatus 6 is returned to the high-boiling separation column 5. The bottom liquid 27 of the high-boiling separation column 5 contains a large amount of Michael adducts of (meth)acrylic acid, and therefore, when it is returned to the decomposition apparatus 6 to decompose the Michael adducts of (meth)acrylic acid and the liquid 28 obtained from the decomposition apparatus 6 is returned to the high-boiling separation column 5, yield of (meth)acrylic acid as a whole process can be increased. A part of the liquid 28 obtained from the decomposition apparatus 6 may be discharged out of the system for suppressing concentration of impurities in the process.

In FIGS. 2 to 4, process flows different from that in FIG. 1 are shown. The process flow shown in FIG. 2 is different from the process flow shown in FIG. 1 in the position where the refining residue 25 is returned to the low-boiling separation column 3. In the process flow of FIG. 2, the refining residue 25 discharged from the crystallizer 4A is returned to the bottom part of the low-boiling separation column 3, and as the refining residue 25 is returned to the bottom of the low-boiling separation column 3 in this manner, the ratio of changing a glyoxal compound to another compound that does not affect the generation of a polymer of methacrylic acid is increased in the low-boiling separation column 3, and as a result, generation of a polymer of (meth)acrylic acid can be further suppressed in the low-boiling separation column 3.

The process flows shown in FIGS. 3 and 4 are different from the process flows shown in FIGS. 1 and 2 in that a distillation column 4B is used as the purification apparatus 4. The crude (meth)acrylic acid 14 withdrawn from the low-boiling separation column 3 is introduced into a middle part of the distillation column 4B, the purified (meth)acrylic acid 15 is withdrawn from a top part of the column, and the refining residue 25 containing a glyoxal compound is withdrawn from a bottom part of the column as distilling residue. In FIG. 3, the refining residue 25 is returned to the middle part of the low-boiling separation column 3 (in detail, a position which is located closer to the bottom side of the column than the supply port of the (meth)acrylic acid-containing liquid), and in FIG. 4, the refining residue 25 is returned to the bottom part of the low-boiling separation column 3. Also in the case where the distillation column 4B is used as the purification apparatus 4, generation of a polymer of (meth)acrylic acid caused by a glyoxal compound in the low-boiling separation column 3 can be suppressed.

This application claims priority to Japanese Patent Application No. 2017-103849, filed on May 25, 2017. All of the contents of the Japanese Patent Application No. 2017-103849, filed on May 25, 2017, are incorporated by reference herein.

EXAMPLES

The present invention will be hereinafter described more specifically by reference to Examples; however, the present invention is not limited to these Examples. In the below description, the term "%" represents "mass %" unless otherwise noted.

Production Example 1

Acrylic acid was produced according to the process flow shown in FIG. 2. A raw material gas containing propylene and molecular oxygen was supplied to a catalytic gas phase reactor to conduct catalytic gas phase oxidation, thereby obtaining an acrylic acid-containing gas. The acrylic acid-containing gas was introduced into a collection column from a bottom part thereof, and a collection solvent (acrylic acid-containing water: acrylic acid concentration of about 1.6%) was supplied to the collection column from a top part thereof to make the acrylic acid-containing gas absorbed into the collection solvent, thereby obtaining an acrylic acid-containing liquid containing 94.2% of acrylic acid, 1.9% of acetic acid, 2.1% of water, and 0.092% of glyoxal.

The acrylic acid-containing liquid obtained from the collection column was introduced into a low-boiling separation column at 12.6 kg/h, thereby conducting distillation of the acrylic acid-containing liquid, and crude acrylic acid containing 99.2% of acrylic acid, 0.07% of acetic acid and 0.01% of water was withdrawn from a middle part of the column at 14.1 kg/h. The low-boiling separation column had an inner diameter of 108.3 mm and was provided with sieve trays of 60 stages at an interval of 113 mm, a supply port for the acrylic acid-containing liquid provided at the 15th stage from the top of the column, and an outlet port for the crude acrylic acid provided at the 39th stage from the top of the column. At the top part of the column, the temperature was 59° C. and the pressure was 6.7 kPa, and at the bottom of the column, the temperature was 87° C. and the pressure was 14 kPa. A low-boiling fraction distilled from the top part of the low-boiling separation column was condensed by a condenser, a part of it was returned to the top part of the low-boiling separation column, and the other part was returned to the collection column to be used as a part of the collection solvent.

From the bottom part of the low-boiling separation column, a bottom liquid containing 64.7% of acrylic acid, 0.03% of acetic acid and 0.01% of water was withdrawn and introduced into a dimer decomposition apparatus to decompose acrylic acid dimer (Michael adducts). In the dimer decomposition apparatus, pyrolysis was performed under the conditions of an internal temperature of the pyrolysis tank of 140° C. and a retention time of 30 hours, and a distillate from the dimer decomposition apparatus was returned to the bottom part of the low-boiling separation column via a high-boiling separation column. The distillate from the high-boiling separation column (containing 95.4% of acrylic acid, 0.6% of acetic acid, 1.5% of water, 0.21% of glyoxal) was returned to the low-boiling separation column at 1.1 kg/h.

The crude acrylic acid withdrawn from the middle part of the low-boiling separation column was introduced into a crystallizer to be further purified. The crystallizer was provided with a metallic crystallization tube, which had a length of 6 m and an inner diameter of 70 mm, and a reservoir (a collector part) at a lower part of the crystallizer. A circulation path connecting the lower part of the crystallizer (the reservoir) to the upper part of the crystallizer (the top of the crystallization tube) was mounted on the crystallizer and provided with a circulation pump. The crystallizer was configured such that a liquid in the reservoir was able to be transferred to the upper part of the tube by the circulation pump and made to flow downward on the inner surface of the crystallization tube in a form of falling film. A double-layered jacket was provided on the outer surface of the crystallization tube and the jacket was controlled so as to keep a constant temperature by a thermostat. The crude acrylic acid was supplied to the lower part of the crystallizer, and made to flow downward on the inner surface of the crystallization tube in the form of falling film while being circulated between the crystallizer and circulation path. Temperature of the jacket was adjusted to be lower than the melting point of acrylic acid, and about 60 mass % to 90 mass % of the crude acrylic acid supplied to the crystallizer was crystallized on the inner surface of the crystallization tube. Then, the circulation pump was stopped and the temperature of the jacket was raised to higher than the melting point of the acrylic acid crystal, whereby about 2 mass % to 5 mass % of the acrylic acid crystal was melted. Thus obtained melt (sweated liquid) was discharged from the crystallizer as a refining residue (crystallizing residue) together with an uncrystallized residual mother liquid obtained in the crystallization. Subsequently, the remaining acrylic acid crystal was melted to obtain acrylic acid melt. By performing the crystallization operation in this manner, purified acrylic acid having an acrylic acid concentration of 99.9% and a glyoxal concentration of less than 0.01% (below the detection limit) was obtained. The refining residue (crystallizing residue) discharged from the crystallizer contained 98.7% of acrylic acid, 0.2% of acetic acid, 0.4% of water and 0.14% of glyoxal, and was returned to the bottom part (below the shelf of the 60th stage) of the low-boiling separation column at 4.5 kg/h.

In Production Example 1, facilities including the low-boiling separation column were able to be stably operated during the operation period of 2 weeks, and on the equipment inspection after the operation period, a polymer of acrylic acid was not confirmed in the low-boiling separation column As the balance (mass balance) of the glyoxal compound in the low-boiling separation column was measured, the conversion ratio of the glyoxal compound was 17%.

Production Example 2

Acrylic acid was produced according to the process flow shown in FIG. 1. Acrylic acid was produced in the same manner as in Production Example 1 except that the refining residue (crystallizing residue) discharged from the crystallizer was returned to the 50th stage, which was the middle part of the column, of the low-boiling separation column. In Production Example 2, facilities including the low-boiling separation column were able to be stably operated during the operation period of 2 weeks, and on the equipment inspection after the operation period, a polymer of acrylic acid was not confirmed in the low-boiling separation column. The conversion ratio of the glyoxal compound was 12%.

Production Example 3

Acrylic acid was produced according to the process flow shown in FIG. 1. Acrylic acid was produced in the same manner as in Production Example 1 except that the refining residue (crystallizing residue) discharged from the crystallizer was returned to the 35th stage, which was the middle part of the column, of the low-boiling separation column. In Production Example 3, facilities including the low-boiling separation column were able to be stably operated during the operation period of 2 weeks, however, as a result of the equipment inspection, it was confirmed that a polymer of (meth)acrylic acid was formed at a lower part of the supply port for the acrylic acid-containing liquid in the low-boiling separation column. The conversion ratio of the glyoxal compound was 8%.

Production Example 4

Acrylic acid was produced according to the process flow shown in FIG. 4. Acrylic acid was produced in the same manner as in Production Example 1 except that: the crude acrylic acid withdrawn from the low-boiling separation column was introduced into a distillation column from the middle part of the column to be subjected to refinement, and purified acrylic acid was withdrawn from the top part of the distillation column and the refining residue withdrawn from the bottom part of the distillation column was returned to the bottom part (below the shelf of the 60th stage) of the low-boiling separation column. The refining residue withdrawn from the bottom part of the distillation column contained 36.0% of acrylic acid, 0.2% of acetic acid, 0.0% of water and 0.02% of glyoxal, and was returned to the low-boiling separation at 4.5 kg/h. In Production Example 4, facilities including the low-boiling separation column were able to be operated stably during the operation period of 2 weeks, and on the equipment inspection after the operation period, a polymer of acrylic acid was not confirmed in the low-boiling separation column. The conversion ratio of the glyoxal compound was 17%.

Production Example 5

Acrylic acid was produced in the same manner as in Production Example 1 except that the refining residue (crystallizing residue) discharged from the crystallizer was returned to the low-boiling separation column through the supply port for the acrylic acid-containing liquid in the low-boiling separation column. In Production Example 5, pressure loss in the low-boiling separation column increased in 10 days from the start of operation, and the low-boiling separation column could not be operated stably. As a result of equipment inspection, it was confirmed that a polymer of (meth)acrylic acid was formed at a lower part of the supply port for the acrylic acid-containing liquid in the low-boiling separation column. The conversion ratio of the glyoxal compound was 5%.

Production Example 6

Acrylic acid was produced in the same manner as in Production Example 5 except that: glyoxal was added to the acrylic acid-containing liquid obtained from the collection column to adjust the glyoxal concentration to 0.170%, and the resultant was introduced into the low-boiling separation column at 12.6 kg/h, thereby conducting distillation of the acrylic acid-containing liquid. In Production Example 6, pressure loss in the low-boiling separation column increased in 8 days from the start of operation, and the low-boiling separation column could not be operated stably. As a result of equipment inspection, it was confirmed that a polymer of (meth)acrylic acid was formed at a lower part of the supply port for the acrylic acid-containing liquid in the low-boiling separation column. The conversion ratio of the glyoxal compound was 5%.

REFERENCE SIGNS LIST

1: reactor
2: collection column
3: low-boiling separation column
4: purification apparatus, 4A: crystallizer, 4B: distillation column
5: high-boiling separation column
6: (meth)acrylic acid dimer decomposition apparatus
11: (meth)acrylic acid production raw material
12: (meth)acrylic acid-containing gas
13: (meth)acrylic acid-containing liquid
14: crude (meth)acrylic acid
15: purified (meth)acrylic acid
21: collection solvent
22: collection column exhaust gas
23: low-boiling fraction
24: bottom liquid of the low-boiling separation column
25: refining residue (crystallizing residue or distillation residue)
26: distillate from the high-boiling separation column
27: bottom liquid of the high-boiling separation column
28: distillate from the (meth)acrylic acid dimer decomposition apparatus

The invention claimed is:
1. A method for producing (meth)acrylic acid, the method comprising:
a step of obtaining a (meth)acrylic acid-containing gas by subjecting a (meth)acrylic acid production raw material to a catalytic gas phase oxidation reaction;
a step of obtaining a (meth)acrylic acid-containing liquid by bringing the (meth)acrylic acid-containing gas into contact with a collection solvent and/or condensing the (meth)acrylic acid-containing gas by cooling;
a step of obtaining crude (meth)acrylic acid by introducing the (meth)acrylic acid-containing liquid into a low-boiling separation column;
a step of obtaining purified (meth)acrylic acid and a refining residue containing a glyoxal compound by purifying the crude (meth)acrylic acid; and
a step of returning at least a part of the refining residue to the low-boiling separation column;
wherein the returning position of the refining residue to the low-boiling separation column is located closer to the bottom side of the low-boiling separation column than the supply port of the (meth)acrylic acid-containing liquid.
2. The method for producing (meth)acrylic acid according to claim 1, wherein
the crude (meth)acrylic acid is introduced into a crystallizer and purified, and the refining residue is obtained as a crystallizing residue.
3. The method for producing (meth)acrylic acid according to claim 1, wherein
the crude (meth)acrylic acid is withdrawn from an outlet port at a position that is intermediate of the top side and the bottom side of the low-boiling separation column, and
the returning position of the refining residue to the low-boiling separation column is located closer to the bottom side of the low-boiling separation column than the outlet port.
4. The method for producing (meth)acrylic acid according to claim 1, wherein
the returning position of the refining residue to the low-boiling separation column is located at a bottom part of the low-boiling separation column.
5. The method for producing (meth)acrylic acid according to claim 1, wherein the crude (meth)acrylic acid is withdrawn from an outlet port at a position that is intermediate of the top side and the bottom side of the low-boiling separation column, and a bottom liquid is withdrawn from the bottom part of the low-boiling separation column and introduced into a high-boiling separation column.

6. The method for producing (meth)acrylic acid according to claim 5, wherein a bottom liquid is withdrawn from a bottom part of the high-boiling separation column and introduced into a (meth)acrylic acid dimmer decomposition apparatus.

* * * * *